(12) United States Patent
Shohami

(10) Patent No.: US 7,655,616 B2
(45) Date of Patent: Feb. 2, 2010

(54) USE OF IL-18 INHIBITORS FOR TREATING HEAD INJURIES

(75) Inventor: Esther Shohami, Mevasseret Zion (IL)

(73) Assignee: Ares Trading S.A. (CH)

( * ) Notice: Subject to any disclaimer, the term of this patent is extended or adjusted under 35 U.S.C. 154(b) by 189 days.

(21) Appl. No.: 10/478,614

(22) PCT Filed: May 23, 2002

(86) PCT No.: PCT/EP02/05666

§ 371 (c)(1),
(2), (4) Date: Apr. 5, 2004

(87) PCT Pub. No.: WO02/096456

PCT Pub. Date: Dec. 5, 2002

(65) Prior Publication Data

US 2004/0191247 A1 Sep. 30, 2004

(30) Foreign Application Priority Data

May 25, 2001 (EP) .................................. 01112067

(51) Int. Cl.
*A61K 38/00* (2006.01)
(52) U.S. Cl. ........................ 514/2; 424/134.1; 530/350; 530/351
(58) Field of Classification Search ........................ None
See application file for complete search history.

(56) References Cited

U.S. PATENT DOCUMENTS 6,566,543 B2 * 5/2003 Mechoulam et al. ........ 554/227
2002/0098185 A1 * 7/2002 Sims et al. ............... 424/145.1

FOREIGN PATENT DOCUMENTS

WO          WO 0185201 A     11/2001

OTHER PUBLICATIONS

Fassbender, K., et al. (1999), *Neurology, Lippincott, Williams & Wilkins*, 53:1104-1106.
Altschul, et al., *J. Mol. Biol.*, 215:403-410 (1990).
Altschul, et al., *Nucleic Acids Research*, 25:3389-3402 (1997).
Chen, et al., *J. of Neuro.*, 13:557-568 (1996).
Conti, et al., *Mol. Brain Res.*, 67:46-52 (1999).
Conti, et al., *J. of Bio. Chem.*, 272:2035-2037 (1997).
Culhane, et al., *Mol. Phsy.*, 3:362-366 (1998).
Devereux, et al., *Nuc. Acids Res.*, 12:387-395 (1984).
DiDonato, et al., *Nature*, 388:548-554 (1997).
Elliott, et al., *Lancet*, 344:1125-1127 (1994).
Jander, et al., *Jour. of Neuro.*, 91:93-99 (1998).
Jennett, et al., *Lancet*, 480-484 (1975).
Izaki, *Tohoku University, Faculty of Agriculture, Department of Agrochemistry*, 6:729-742 (1978).
Kim, et al., *PNAS*, 97:1190-1195 (2000).
Knight, et al., *Mol. Imm.*, 30:1443-1453 (1993).
Kossmann, et al., *J. of Cer. Blood Flow and Met.*, 17:280-289 (1997).
Maliszewski, et al., *Jour. of Imm.*, 144:3028-3033 (1990).
Morganti-Kossman, et al., *Mol. Psy.*, 2:133-136 (1997).
Miscallef, et al., *Eur. J. Imm.*, 26:1647-1651 (1996).
Nakamura, et al., *Inf. and Imm.*, 57:590-595 (1989).
Novick, et al., *Imm.*, 10:127-136 (1999).
Okamura, et al., *Inf and Imm.*, 63:3966-3972 (1995).
Parnett, et al., *Jour. of Bio. Chem.*, 271:3967-3970 (1996).
Pearson, *Met. of Enzy.*, 183:63-98 (1990).
Pearson, et al., *Proc. Natl. Acad. Sci.*, 85:2444-2448 (1988).
Prinz, et al., *Jour. of Neuro.*, 72:2215-2218 (1999).
Rothe, et al., *Jour. of Clin. Inves.*, 99:469-474 (1997).
Scherbel, et al., *Proc. Natl. Acad. Sci.*, 96:8721-8726 (1999).
Shohami, et al., *Cyt. and Growth Fac. Rev.*, 10:119-130 (1999).
Shohami, et al., *Jour. of Cer. Blood Flow and Med.*, 17:1007-1019 (1997).
Stahel, et al., *Jour. of Cer. Blood Flow and Met.*, 20:369-380 (2000).
Teasdale, et al., *Lancet*, 81-84 (1974).
Ushio, et al., *Jour. of Imm.*, 156:4274-4279 (1996).
Whalen, et al., *Crit. Care Med.*, 28:929-934 (2000).
Wheeler, et al., *Mol. Brain Res.*, 77:290-293 (2000).
Yoshimoto, et al., *Jour. of Imm.*, 161:3400-3407 (1998).

* cited by examiner

*Primary Examiner*—Dong Jiang
(74) *Attorney, Agent, or Firm*—Nixon Peabody LLP

(57) ABSTRACT

The invention relates to the use of inhibitors of IL-18 in the preparation of a medicament for treatment and/or prevention of central nervous system injury, in particular of traumatic head injury.

13 Claims, 3 Drawing Sheets time after closed head injury

USE OF IL-18 INHIBITORS FOR TREATING HEAD INJURIES

CROSS-REFERENCE TO RELATED APPLICATIONS

This application is the U.S. National Phase Entry Under 35 U.S.C. 371 of International Application No. PCT/EP02/05666, filed May 23, 2002 which designated the U.S.

FIELD OF THE INVENTION

The present invention is in the field of pathological conditions of the brain. More specifically, it relates to the use of an inhibitor of IL-18 for the treatment and/or prevention of central nervous system (CNS) injury, in particular traumatic brain injury.

BACKGROUND OF THE INVENTION

In 1989, an endotoxin-induced serum activity that induced interferon-γ (IFN-γ) obtained from mouse spleen cells was described (Nakamura et al., 1989). This serum activity functioned not as a direct inducer of IFN-γ but rather as a co-stimulant together with IL-2 or mitogens. An attempt to purify the activity from post-endotoxin mouse serum revealed an apparently homogeneous 50-55 kDa protein. Since other cytokines can act as co-stimulants for IFN-γ production, the failure of neutralizing antibodies to IL-1, IL4, IL-5, IL-6, or TNF to neutralize the serum activity suggested it was a distinct factor. In 1995, the same scientists demonstrated that the endotoxin-induced co-stimulant for IFN-γ production was present in extracts of livers from mice pre-conditioned with P. acnes (Okamura et al., 1995). In this model, the hepatic macrophage population (Kupffer cells) expand and in these mice, a low dose of bacterial lipopolysaccharide (LPS), which in non-preconditioned mice is not lethal, becomes lethal. The factor, named IFN-γ-inducing factor (IGIF) and later designated interleukin-18 (IL-18), was purified to homogeneity from 1,200 grams of P. acnes-treated mouse livers. Degenerate oligonucleotides derived from amino acid sequences of purified IL-18 were used to clone a murine IL-18 cDNA. IL-18 is an 18-19 kDa protein of 157 amino acids, which has no obvious similarities to any peptide in the databases. Messenger RNAs for IL-18 and interleukin-12 (IL-12) are readily detected in Kupffer cells and activated macrophages. Recombinant IL-18 induces IFN-gamma more potently than does IL-12, apparently through a separate pathway (Micallef et al., 1996). Similar to the endotoxin-induced serum activity, IL-18 does not induce IFN-γ by itself, but functions primarily as a co-stimulant with mitogens or IL-2. IL-18 enhances T cell proliferation, apparently through an IL-2-dependent pathway, and enhances Th1 cytokine production in vitro and exhibits synergism when combined with IL-12 in terms of enhanced IFN-γ production (Maliszewski et al., 1990).

After the murine form was cloned, the human cDNA sequence for IL-18 was reported in 1996 (Ushio et al., 1996).

By cloning IL-18 from affected tissues and studying IL-18 gene expression, a close association of this cytokine with an autoimmune disease was found. The non-obese diabetic (NOD) mouse spontaneously develops autoimmune insulitis and diabetes, which can be accelerated and synchronized by a single injection of cyclophosphamide. IL-18 mRNA was demonstrated by reverse transcriptase PCR in NOD mouse pancreas during early stages of insulitis. Levels of IL-18 mRNA increased rapidly after cyclophosphamide treatment and preceded a rise in IFN-γ mRNA, and subsequently diabetes. Interestingly, these kinetics mimic that of IL-12-p40 mRNA, resulting in a close correlation of individual mRNA levels. Cloning of the IL-18 cDNA from pancreas RNA followed by sequencing revealed identity with the IL-18 sequence cloned from Kupffer cells and in vivo pre-activated macrophages. Also NOD mouse macrophages responded to cyclophosphamide with IL-18 gene expression while macrophages from Balb/c mice treated in parallel did not. Therefore, IL-18 expression is abnormally regulated in autoimmune NOD mice and closely associated with diabetes development (Rothe et al., 1997).

IL-18 plays a potential role in immunoregulation or in inflammation by augmenting the functional activity of Fas ligand on Th1 cells (Conti et al., 1997). IL-18 is also expressed in the adrenal cortex and therefore might be a secreted neuro-immunomodulator, playing an important role in orchestrating the immune system following a stressful experience (Chater, 1986).

In vivo, IL-18 is formed by cleavage of pro-IL-18, and its endogenous activity appears to account for IFN-γ production in P. acnes and LPS-mediated lethality. Mature IL-18 is produced from its precursor by the IL-1β converting enzyme (IL-1beta-converting enzyme, ICE, caspase-1).

The IL-18 receptor consists of at least two components, co-operating in ligand binding. High- and low-affinity binding sites for IL-18 were found in murine IL-12 stimulated T cells (Yoshimoto et al., 1998), suggesting a multiple chain receptor complex. Two receptor subunits have been identified so far, both belonging to the IL-1 receptor family (Parnet et al., 1996). The signal transduction of IL-18 involves activation of NF-κB (DiDonato et al., 1997).

Recently, a soluble protein having a high affinity for IL-18 has been isolated from human urine, and the human and mouse cDNAs were described (Novick et al., 1999; WO 99/09063). The protein has been designated IL-18 binding protein (IL-18BP).

IL-18BP is not the extracellular domain of one of the known IL18 receptors, but a secreted, naturally circulating protein. It belongs to a novel family of secreted proteins. The family further includes several Poxvirus-encoded proteins which have a high homology to IL-18BP (Novick et al., 1999). IL-18BP is constitutively expressed in the spleen, belongs to the immunoglobulin superfamily, and has limited homology to the IL-1 type II receptor. Its gene was localized on human chromosome 11q13, and no exon coding for a transmembrane domain was found in an 8.3 kb genomic sequence (Novick et al., 1999).

Four human and two mouse isoforms of IL-18BP, resulting from mRNA splicing and found in various cDNA libraries and have been expressed, purified, and assessed for binding and neutralization of IL-18 biological activities (Kim et al., 2000). Human IL-18BP isoform a (IL-18BPa) exhibited the greatest affinity for IL-18 with a rapid on-rate, a slow off-rate, and a dissociation constant (K(d)) of 399 pM. IL-18BPc shares the Ig domain of IL-18BPa except for the 29 C-terminal amino acids; the K(d) of IL-18BPc is 10-fold less (2.94 nM). Nevertheless, IL-18BPa and IL-18BPc neutralize IL-18>95% at a molar excess of two. IL-18BPb and IL-18BPd isoforms lack a complete Ig domain and lack the ability to bind or neutralize IL-18. Murine IL-18BPc and IL-18BPd isoforms, possessing the identical Ig domain, also neutralize >95% murine IL-18 at a molar excess of two. However, murine IL-18BPd, which shares a common C-terminal motif with human IL-18BPa, also neutralizes human IL-18. Molecular modelling identified a large mixed electrostatic and hydrophobic binding site in the Ig domain of IL-18BP, which could account for its high affinity binding to the ligand (Kim et al., 2000).

Traumatic brain injury (TBI), also simply called head injury, or closed head injury (CHI), refers to an injury of the central nervous system where there is damage to the brain caused by an external blow to the head. It mostly happens during car or bicycle accidents, but may also occur as the result of near drowning, heart attack, stroke and infections. This type of traumatic brain injury would usually result due to the lack of oxygen or blood supply to the brain, and therefore can be referred to as an "anoxic injury".

Closed head injury occurs when there is a blow to the head as in a motor vehicle accident or a fall. In this case, the skull hits a stationary object and the brain, which is inside the skull, turns and twists on its axis (the brain stem), causing localized or widespread damage. Also, the brain, a soft mass surrounded by fluid that allows it to "float," may rebound against the skull resulting in further damage.

There may be a period of unconsciousness immediately following the trauma, which may last minutes, weeks or months. Due to the twisting and rebounding, the traumatically brain injured patient usually receives damage or bruising to many parts of the brain. This is called diffuse damage, or "non-missile injury" to the brain. The types of brain damages occurring in non-missile injuries may be classified as either primary or secondary.

Primary brain damage occurs at the time of injury, mainly at the sites of impact, in particular when a skull fraction is present. Large contusions may be associated with an intracerebral haemorrhage, or accompanied by cortical lacerations. Diffuse axonal injuries occur as a result of shearing and tensile strains of neuronal processes produced by rotational movements of the brain within the skull. There may be small heamorrhagic lesions or diffuse damage to axons, which can only be detected microscopically.

Secondary brain damage occurs as a result of complications developing after the moment of injury. They include intracranial hemorrhage, traumatic damage to extracerebral arteries, intracranial herniation, hypoxic brain damage or meningitis.

An "open head injury" is a visible assault to the head and may result from a gunshot wound, an accident or an object going through the skull into the brain ("missile injury to the brain"), This type of head injury is more likely to damage a specific area of the brain.

So called "mild brain injury" may occur with no loss of consciousness and possibly only a dazed feeling or confused state lasting a short time. Although medical care administered may be minimal, persons with brain injury without coma may experience symptoms and impairments similar to those suffered by the survivor of a coma injury.

In response to the trauma, changes occur in the brain, which require monitoring to prevent further damage. The brain's size frequently increases after a severe head injury. This is called brain swelling and occurs when there is an increase in the amount of blood to the brain. Later in the illness water may collect in the brain, which is called brain edema. Both brain swelling and brain edema result in excessive pressure in the brain called intracranial pressure ("ICP").

Coma is the prolonged period of unconsciousness immediately following the traumatic head injury.

There are several levels of coma. Coma levels can be measured by the progression of responsiveness of the head injured person. In the acute phase of head injury the "Glasgow Coma Scale" is used. As the patient improves or stabilizes, the "Rancho Los Amigos Scale" is used which measures levels of cognitive (understanding and reasoning) thinking.

Brain injury frequently results in persisting debility, such as post-traumatic epilepsy, persistent vegetative state, or post-traumatic dementia.

Spinal cord injury is another type of CNS injury. Spinal cord injuries account for the majority of hospital admissions for paraplegia and tetraplegia. Over 80% occur as a result of road accidents. Two main groups of injury are recognized clinically: open injuries and closed injuries.

Open injuries cause direct trauma of the spinal cord and nerve roots. Perforating injuries can cause extensive disruption and haemorrhage. Closed injuries account for most spinal injuries and are usually associated with a fracture/dislocation of the spinal column, which is usually demonstrable radiologically. Damage to the cord depends on the extent of the bony injuries and can be considered in two main stages: Primary damage, which are contusions, nerve fibre transections and heamorrhagic necrosis, and secondary damage, which are extradural haematoma, infarction, infection and oedema.

Late effects of cord damage include: ascending and descending anterograde degeneration of damaged nerve fibers, post-traumatic syringomelyia, and systemic effects of paraplegia, such as urinary tract and chest infections, pressure sores and muscle wasting.

The pathology of traumatic brain injury is very complex and still poorly understood. Research efforts in the past decade have highlighted an important role of cytokines released systemically and locally within the intrathecal compartment after brain injury, and a dual effect of pro-inflammatory cytokines, such as TNF, IL-6, or IL-8, was hypothesized based on findings of time-dependent beneficial and adverse effects of these mediators (Morganti-Kossmann et al., 1997; Kossmann et al., 1997; Shohami et al., 1999, Scherbel et al., 1999; Whalen et al., 2000). As described above, a recently discovered cytokine of the IL-1 family is IL-18. Recent studies have demonstrated that IL-18 is constitutively expressed in the CNS of mice, rats, and humans in vivo (Culhane et al., 1998; Jander and Stoll, 1998; Prinz et al., 1999; Fassbender et al., 1999; Wheeler et al., 2000), as well as in primary cultures of astrocytes and microglia, but not neurons, in vitro (Conti et al., 1999). Increased IL-18 levels were detected in the cerebrospinal fluid (CSF) of patients with inflammatory CNS diseases, such as bacterial meningitis and viral meningoencephalitis, but not in the CSF of multiple sclerosis (MS) patients (Fassbender et al., 1999). In contrast to the finding of generally low intrathecal IL-18 levels in MS patients, increased IL-18 mRNA expression was demonstrated in spinal cords of Lewis rats with experimental autoimmune encephalomyelitis (EAE), the animal model for MS (Jander and Stoll, 1998). The expression and functional significance of IL-18 in neurotrauma has not been investigated until now.

SUMMARY OF THE INVENTION

The present invention relates to the pathophysiological role of IL-18 in CNS diseases. It is based on the finding that the treatment of mice with inhibitors of IL-18, either one hour or three days after experimental closed head injury (CHI), results in an improved recovery and attenuated extent of brain damage as compared to control animals. The invention therefore relates to the use of an IL-18 inhibitor for the manufacture of a medicament for treatment and/or prevention of central nervous system (CNS) injury, and in particular of traumatic brain injury.

The use of combinations of an IL-18 inhibitor with an interferon and/or TNF and/or inhibitors of inflammation and/or anfioxidants are also provided according to the invention. In order to apply gene therapeutic approaches to deliver the IL-18 inhibitor to diseased tissues or cells, further aspects of the invention relate to the use of nucleic acid molecules comprising the coding sequence of an IL-18 inhibitor for the treatment and/or prevention of the CNS injury. The invention also relates to the use of cells genetically engineered to express IL-18 inhibitors for the prevention and/or treatment of CNS injury.

DESCRIPTION OF THE INVENTION

Figure 1:
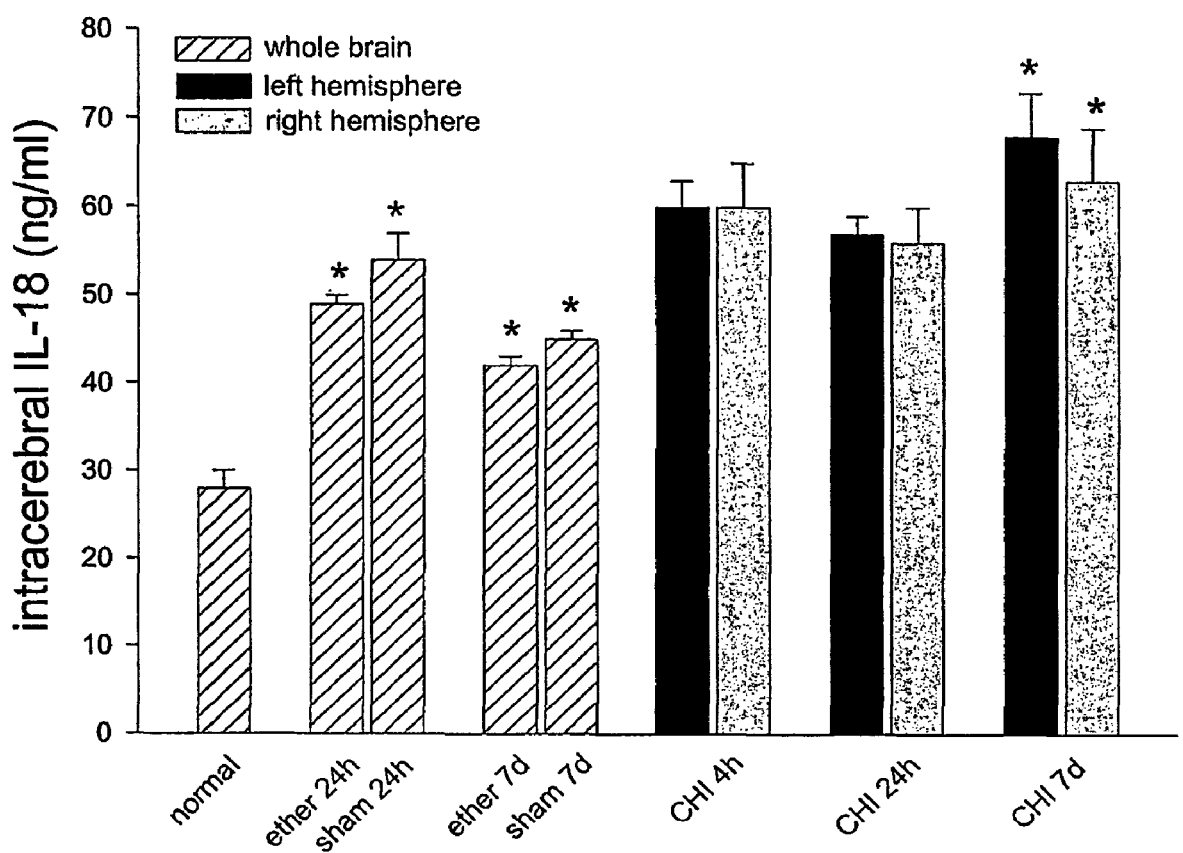
FIG. 1 shows a histogram depicting the serum levels of intracerebral IL-18 (ng/ml) in whole brain (hatched), in the left hemisphere (black) or in the right hemisphere (gray) under different conditions.

The present invention is based on the finding of a statistically significant beneficial effect of an IL-18 inhibitor on the recovery from brain injury in a murine model of closed head injury. In accordance with the present invention, it has further been found that IL-18 is up-regulated in the brain and cerebrospinal fluid after traumatic brain injury, indicating that this pro-inflammatory cytokine plays an important role in the pathogenesis of brain injury.

Therefore, the invention relates to the use of an IL-18 inhibitor for the manufacture of a medicament for treatment and/or prevention of central nervous system (CNS) injury.

The invention further relates to the use of an IL-18 inhibitor for the manufacture of a medicament for treatment and/or prevention of complications and late effects of CNS injury.

In preferred embodiments of the invention, the CNS injury is traumatic brain injury or closed head injury.

In a further preferred embodiment, the CNS injury is spinal cord injury.

In yet a further yet a further preferred embodiment of the invention, the brain injury is of vascular origin.

Within the context of the present invention, the expression "central nervous system injury" or "CNS injury" relates to any injury to the brain or spinal cord, regardless of the age at onset, or the underlying cause. The underlying cause may e.g. be mechanical, or an infection. CNS injury and its clinical symptoms and implications have been described in detail in the "Background of the invention". CNS injury includes e.g. trauma, or any other damage of the brain or spinal cord, and it may also be called neurotrauma.

Brain injury may for example include or result in any one, or more, of the following: 1. Attention impairment; 2. cognition impairment; 3. language impairment; 4. memory impairment; 5. conduct disorder; 6. motor disorder; 6. any other neurological dysfunction.

Spinal cord injury may for example result in paraplegia or tetraplegia.

Complications or late effects of CNS injury may also be treated and/or prevented in accordance with the present invention. Complications and late effects of brain injuries have been described above in the "Background of the invention". They include, but are not limited to, coma, meningitis, post-traumatic epilepsy, post-traumatic dementia, degeneration of nerve fibers, or post-traumatic syringomyelia, or hemorrhage, for example.

The present invention also relates to the use of IL-18 inhibitors for the preparation of a medicament for treatment and/or prevention of any injury to the brain that is vascular in origin, such as hypoxic brain damage with cerebral infarction, ischemia, cerebrovascular accident, or stroke.

The terms "treating" and "preventing", as used herein, should be understood as partially or totally preventing, inhibiting, attenuating, ameliorating or reversing one or more symptoms or cause(s) of CNS injury, as well as symptoms, diseases or complications accompanying CNS injury. When "treating" CNS injury, the substances according to the invention are given after onset of the disease, "prevention" relates to administration of the substances before signs of disease can be noted in the patient.

Treatment of CNS injury is preferred in accordance with the present invention. Preferably, in order to treat CNS injury, the IL-18 inhibitor is administered as soon as possible after CNS injury, e.g. within the first hour after the injury. However, as shown in the Examples below, one IL-18 inhibitor was shown to exert its beneficial effect on brain injury even when administered three days after brain injury occurred. Therefore, in order to treat CNS injury, it is preferred to administer the IL-18 inhibitor within three days from the injury.

The term "inhibitor of IL-18" within the context of this invention, refers to any molecule modulating IL-18 production and/or action in such a way that IL-18 production and/or action is attenuated, reduced, or partially, substantially or completely prevented or blocked. The term "IL-18 inhibitor" is meant to encompass inhibitors of IL-18 production, as well as of inhibitors of IL-18 action.

An inhibitor of production can be any molecule negatively affecting the synthesis, processing or maturation of IL-18. The inhibitors considered according to the invention can be, for example, suppressors of gene expression of the interleukin IL-18, antisense mRNAs reducing or preventing the transcription of the IL-18 mRNA or leading to degradation of the mRNA, proteins impairing correct folding, or partially or substantially preventing secretion of IL-18, proteases degrading IL-18, once it has been synthesized, inhibitors of proteases cleaving pro-IL-18 in order to generate mature IL-18, such as inhibitors of caspase-1, and the like.

An inhibitor of IL-18 action can be an IL-18 antagonist, for example. Antagonists can either bind to or sequester the IL-18 molecule itself with sufficient affinity and specificity to partially or substantially neutralize the IL-18 or IL-18 binding site(s) responsible for IL-18 binding to its ligands (like, e.g. to its receptors). An antagonist may also inhibit the IL-18 signaling pathway, which is activated within the cells upon IL-18 binding to its receptor.

Inhibitors of IL-18 action may also be soluble IL-18 receptors or molecules mimicking the receptors, or agents blocking the IL-18 receptors, or IL-18 antibodies, such as polyclonal or monoclonal antibodies, or any other agent or molecule preventing the binding of IL-18 to its targets, thus diminishing or preventing triggering of the intra- or extracellular reactions mediated by IL-18.

In a preferred embodiment of the present invention, the inhibitor of IL-18 is selected from inhibitors of caspase-1 (ICE), antibodies directed against IL-18, antibodies directed against any of the IL-18 receptor subunits, inhibitors of the IL-18 signaling pathway, antagonists of IL-18 which compete with IL-18, or bind to, and block the IL-18 receptor, and IL-18 binding proteins, isoforms, muteins, fused proteins, functional derivatives, active fractions or circularly permutated derivatives, or salts thereof.

The term "IL-18 binding proteins" is used herein synonymously with "IL18BP". It comprises IL-18 binding proteins as defined in WO 99/09063 or in Novick et al., 1999, including splice variants and/or isoforms of IL-18 binding proteins, as defined in Kim et al., 2000. In particular, human isoforms a and c of IL-18BP are useful in accordance with the presence invention. The proteins useful according to the present invention may be glycosylated or non-glycosylated, they may be derived from natural sources, such as urine, or they may preferably be produced recombinantly. Recombinant expression may be carried out in prokaryotic expression systems like E. coli, or in eukaryotic, and preferably in mammalian, expression systems. A cell line particularly well suited for the IL-18 inhibitors of the present invention is the Chinese hamster ovary (CHO) cell.

Recombinant production of the IL-18 inhibitor, when recombinantly expressed in mammalian cells or cell lines, may preferably be carried out in serum free cell culture medium.

As used herein the term "muteins" refers to analogs of an IL-18BP, or analogs of a viral IL-18BP, in which one or more of the amino acid residues of a natural IL-18BP or viral IL-18BP are replaced by different amino acid residues, or are deleted, or one or more amino acid residues are added to the natural sequence of an IL-18BP, or a viral IL-18BP, without reducing considerably the activity of the resulting products as compared with the wild type IL-18BP or viral IL-18BP. These muteins are prepared by known synthesis and/or by site-directed mutagenesis techniques, or any other known technique suitable therefor.

Any such mutein preferably has a sequence of amino acids sufficiently duplicative of that of an IL-18BP, or sufficiently duplicative of a viral IL-18BP, such as to have substantially similar activity to IL-18BP. One activity of IL-18BP is its capability of binding IL-18. As long as the mutein has substantial binding activity to IL-18, it can be used in the purification of IL-18, such as by means of affinity chromatography, and thus can be considered to have substantially similar activity to IL-18BP. Thus, it can be determined whether any given mutein has an activity substantially similar to IL-18BP by means of routine experimentation comprising subjecting such a mutein, e.g., to a simple sandwich competition assay to determine whether or not it binds to an appropriately labeled IL-18, such as radioimmunoassay or ELISA assay. Simple functional assays for assessing the biological activity of IL-18BP were described in detail in WO 99/09063, e.g. in examples 2 (binding to IL-18 as assessed by cross-linking) or 5 (inhibition of IL-18 induced INF-gamma induction in mononuclear blood cells).

In a preferred embodiment, any such mutein has at least 40% identity or homology with the sequence of either an IL-18BP or a virally-encoded IL-18BP homologue. More preferably, it has at least 50%, at least 60%, at least 70%, at least 80% or, most preferably, at least 90% identity or homology thereto.

Muteins of IL-18BP polypeptides or muteins of viral IL-18BPs, which can be used in accordance with the present invention, or nucleic acid coding therefor, include a finite set of substantially corresponding sequences as substitution peptides or polynucleotides which can be routinely obtained by one of ordinary skill in the art, without undue experimentation, based on the teachings and guidance presented herein.

Muteins in accordance with the present invention include proteins encoded by a nucleic acid, such as DNA or RNA, which hybridizes to DNA or RNA, which encodes the IL-18 inhibitor, in accordance with the present invention, under moderately or highly stringent conditions. The term "stringent conditions" refers to hybridization and subsequent washing conditions, which those of ordinary skill in the art conventionally refer to as "stringent". See Ausubel et al., Current Protocols in Molecular Biology, supra, Interscience, N.Y., §§6.3 and 6.4 (1987, 1992), and Sambrook et al. (Sambrook, J. C., Fritsch, E. F., and Maniatis, T. (1989) Molecular Cloning: A Laboratory Manual, Cold Spring Harbor Laboratory Press, Cold Spring Harbor, N.Y.).

Without limitation, examples of stringent conditions include washing conditions 12-20° C. below the calculated Tm of the hybrid under study in, e.g., 2×SSC and 0.5% SDS for 5 minutes, 2×SSC and 0.1% SDS for 15 minutes; 0.1×SSC and 0.5% SDS at 37° C. for 30-60 minutes and then, a 0.1× SSC and 0.5% SDS at 68° C. for 30-60 minutes. Those of ordinary skill in this art understand that stringency conditions also depend on the length of the DNA sequences, oligonucleotide probes (such as 10-40 bases) or mixed oligonucleotide probes. If mixed probes are used, it is preferable to use tetramethyl ammonium chloride (TMAC) instead of SSC. See Ausubel, supra.

In a preferred embodiment, any such mutein has at least 40% identity or homology with the sequence of SEQ ID NO: 1, 2 or 3 of the annexed sequence listing. More preferably, it has at least 50%, at least 60%, at least 70%, at least 80% or, most preferably, at least 90% identity or homology thereto.

Identity reflects a relationship between two or more polypeptide sequences or two or more polynucleotide sequences, determined by comparing the sequences. In general, identity refers to an exact nucleotide to nucleotide or amino acid to amino acid correspondence of the two polynucleotides or two polypeptide sequences, respectively, over the length of the sequences being compared.

For sequences where there is not an exact correspondence, a "% identity" may be determined. In general, the two sequences to be compared are aligned to give a maximum correlation between the sequences. This may include inserting "gaps" in either one or both sequences, to enhance the degree of alignment. A % identity may be determined over the whole length of each of the sequences being compared (so-called global alignment), that is particularly suitable for sequences of the same or very similar length, or over shorter, defined lengths (so-called local alignment), that is more suitable for sequences of unequal length.

Methods for comparing the identity and homology of two or more sequences are well known in the art. Thus for instance, programs available in the Wisconsin Sequence Analysis Package, version 9.1 (Devereux J et al., 1984), for example the programs BESTFIT and GAP, may be used to determine the % identity between two polynucleotides and the % identity and the % homology between two polypeptide sequences. BESTFIT uses the "local homology" algorithm of Smith and Waterman (1981) and finds the best single region of similarity between two sequences. Other programs for determining identity and/or similarity between sequences are also known in the art, for instance the BLAST family of programs (Altschul S F et al, 1990, Altschul S F et al, 1997, accessible through the home page of the NCBI at www.ncbi.nlm.nih.gov) and FASTA (Pearson W R, 1990; Pearson 1988).

Preferred changes for muteins in accordance with the present invention are what are known as "conservative" substitutions. Conservative amino acid substitutions of IL-18BP polypeptides or proteins or viral IL-18BPs, may include synonymous amino acids within a group which have sufficiently similar physicochemical properties that substitution between members of the group will preserve the biological function of the molecule (Grantham, 1974). It is clear that insertions and deletions of amino acids may also be made in the above-defined sequences without altering their function, particularly if the insertions or deletions only involve a few amino acids, e.g., under thirty, and preferably under ten, and do not remove or displace amino acids which are critical to a functional conformation, e.g., cysteine residues. Proteins and muteins produced by such deletions and/or insertions come within the purview of the present invention.

Preferably, the synonymous amino acid groups are those defined in Table 1. More preferably, the synonymous amino acid groups are those defined in Table 2; and most preferably the synonymous amino acid groups are those defined in Table 3.

TABLE 1

Preferred Groups of Synonymous Amino Acids

| Amino Acid | Synonymous Group |
|---|---|
| Ser | Ser, Thr, Gly, Asn |
| Arg | Arg, Gln, Lys, Glu, His |
| Leu | Ile, Phe, Tyr, Met, Val, Leu |
| Pro | Gly, Ala, Thr, Pro |
| Thr | Pro, Ser, Ala, Gly, His, Gln, Thr |
| Ala | Gly, Thr, Pro, Ala |
| Val | Met, Tyr, Phe, Ile, Leu, Val |
| Gly | Ala, Thr, Pro, Ser, Gly |
| Ile | Met, Tyr, Phe, Val, Leu, Ile |
| Phe | Trp, Met, Tyr, Ile, Val, Leu, Phe |
| Tyr | Trp, Met, Phe, Ile, Val, Leu, Tyr |
| Cys | Ser, Thr, Cys |
| His | Glu, Lys, Gln, Thr, Arg, His |
| Gln | Glu, Lys, Asn, His, Thr, Arg, Gln |
| Asn | Gln, Asp, Ser, Asn |
| Lys | Glu, Gln, His, Arg, Lys |
| Asp | Glu, Asn, Asp |
| Glu | Asp, Lys, Asn, Gln, His, Arg, Glu |
| Met | Phe, Ile, Val, Leu, Met |
| Trp | Trp |

TABLE 2

More Preferred Groups of Synonymous Amino Acids

| Amino Acid | Synonymous Group |
|---|---|
| Ser | Ser |
| Arg | His, Lys, Arg |
| Leu | Leu, Ile, Phe, Met |
| Pro | Ala, Pro |
| Thr | Thr |
| Ala | Pro, Ala |
| Val | Val, Met, Ile |
| Gly | Gly |
| Ile | Ile, Met, Phe, Val, Leu |
| Phe | Met, Tyr, Ile, Leu, Phe |
| Tyr | Phe, Tyr |
| Cys | Cys, Ser |
| His | His, Gln, Arg |
| Gln | Glu, Gln, His |

TABLE 2-continued

More Preferred Groups of Synonymous Amino Acids

| Amino Acid | Synonymous Group |
|---|---|
| Asn | Asp, Asn |
| Lys | Lys, Arg |
| Asp | Asp, Asn |
| Glu | Glu, Gln |
| Met | Met, Phe, Ile, Val, Leu |
| Trp | Trp |

TABLE 3

Most Preferred Groups of Synonymous Amino Acids

| Amino Acid | Synonymous Group |
|---|---|
| Ser | Ser |
| Arg | Arg |
| Leu | Leu, Ile, Met |
| Pro | Pro |
| Thr | Thr |
| Ala | Ala |
| Val | Val |
| Gly | Gly |
| Ile | Ile, Met, Leu |
| Phe | Phe |
| Tyr | Tyr |
| Cys | Cys, Ser |
| His | His |
| Gln | Gln |
| Asn | Asn |
| Lys | Lys |
| Asp | Asp |
| Glu | Glu |
| Met | Met, Ile, Leu |
| Trp | Met |

Examples of production of amino acid substitutions in proteins which can be used for obtaining muteins of IL-18BP polypeptides or proteins, or muteins of viral IL-18BPs, for use in the present invention include any known method steps, such as presented in U.S. Pat. Nos. 4,959,314, 4,588,585 and 4,737,462, to Mark et al; U.S. Pat. No. 5,116,943 to Koths et al., U.S. Pat. No. 4,965,195 to Namen et al; U.S. Pat. No. 4,879,111 to Chong et al; and U.S. Pat. No. 5,017,691 to Lee et al; and lysine substituted proteins presented in U.S. Pat. No. 4,904,584 (Shaw et al).

The term "fused protein" refers to a polypeptide comprising an IL-18BP, or a viral IL-18BP, or a mutein or fragment thereof, fused with another protein, which, e.g., has an extended residence time in body fluids. An IL-18BP or a viral IL-18BP, may thus be fused to another protein, polypeptide or the like, e.g., an immunoglobulin or a fragment thereof.

"Functional derivatives" as used herein cover derivatives of IL-18BPs or a viral IL-18BP, and their muteins and fused proteins, which may be prepared from the functional groups which occur as side chains on the residues or the N- or C-terminal groups, by means known in the art, and are included in the invention as long as they remain pharmaceutically acceptable, i.e. they do not destroy the activity of the protein which is substantially similar to the activity of IL-18BP, or viral IL-18BPs, and do not confer toxic properties on compositions containing it.

These derivatives may, for example, include polyethylene glycol side-chains, which may mask antigenic sites and extend the residence of an IL-18BP or a viral IL-18BP in body fluids. Other derivatives include aliphatic esters of the carboxyl groups, amides of the carboxyl groups by reaction with ammonia or with primary or secondary amines, N-acyl derivatives of free amino groups of the amino acid residues formed with acyl moieties (e.g. alkanoyl or carbocyclic aroyl groups) or O-acyl derivatives of free hydroxyl groups (for example that of seryl or threonyl residues) formed with acyl moieties.

As "active fractions" of an IL-18BP, or a viral IL-18BP, muteins and fused proteins, the present invention covers any fragment or precursors of the polypeptide chain of the protein molecule alone or together with associated molecules or residues linked thereto, e.g., sugar or phosphate residues, or aggregates of the protein molecule or the sugar residues by themselves, provided said fraction has substantially similar activity to IL-18BP.

The term "salts" herein refers to both salts of carboxyl groups and to acid addition salts of amino groups of IL-18 inhibitor molecule, or analogs thereof. Salts of a carboxyl group may be formed by means known in the art and include inorganic salts, for example, sodium, calcium, ammonium, ferric or zinc salts, and the like, and salts with organic bases as those formed, for example, with amines, such as triethanolamine, arginine or lysine, piperidine, procaine and the like. Acid addition salts include, for example, salts with mineral acids, such as, for example, hydrochloric acid or sulfuric acid, and salts with organic acids, such as, for example, acetic acid or oxalic acid. Of course, any such salts must retain the biological activity of OPN relevant to the present invention, i.e., exert a proliferative effect on oligodendrocytes.

In a further preferred embodiment of the invention, the inhibitor of IL-18 is an IL-18 antibody. Anti-IL-18 antibodies may be polyclonal or monoclonal, chimeric, humanized, or even fully human. Recombinant antibodies and fragments thereof are characterized by high affinity binding to IL-18 in vivo and low toxicity. The antibodies which can be used in the invention are characterized by their ability to treat patients for a period sufficient to have good to excellent regression or alleviation of the pathogenic condition or any symptom or group of symptoms related to a pathogenic condition, and a low toxicity.

Neutralizing antibodies are readily raised in animals such as rabbits, goat or mice by immunization with IL-18. Immunized mice are particularly useful for providing sources of B cells for the manufacture of hybridomas, which in turn are cultured to produce large quantities of anti-IL-18 monoclonal antibodies.

Chimeric antibodies are immunoglobulin molecules characterized by two or more segments or portions derived from different animal species. Generally, the variable region of the chimeric antibody is derived from a non-human mammalian antibody, such as murine monoclonal antibody, and the immunoglobulin constant region is derived from a human immunoglobulin molecule. Preferably, both regions and the combination have low immunogenicity as routinely determined (Elliott et al., 1994). Humanized antibodies are immunoglobulin molecules created by genetic engineering techniques in which the murine constant regions are replaced with human counterparts while retaining the murine antigen binding regions. The resulting mouse-human chimeric antibody preferably have reduced immunogenicity and improved pharmacokinetics in humans (Knight et al., 1993).

Thus, in a further preferred embodiment, IL-18 antibody is a humanized IL-18 antibody. Preferred examples of humanized anti-IL-18 antibodies are described in the European Patent Application EP 0 974 600, for example.

In yet a further preferred embodiment, the IL-18 antibody is fully human. The technology for producing human antibodies is described in detail e.g. in WO00/76310, WO99/53049, U.S. Pat. No. 6,162,963 or AU5336100. Fully human antibodies are preferably recombinant antibodies, produced in transgenic animals, e.g. xenomice, comprising all or portions of functional human Ig loci.

In a highly preferred embodiment of the present invention, the inhibitor of IL-18 is an IL-18BP, or an isoform, a mutein, fused protein, functional derivative, active fraction or circularly permutated derivative thereof. These isoforms, muteins, fused proteins or functional derivatives retain the biological activity of IL-18BP, in particular the binding to IL-18, and preferably have essentially at least an activity similar to IL-18BP. Ideally, such proteins have a biological activity which is even increased in comparison to unmodified IL-18BP. Preferred active fractions have an activity which is better than the activity of IL-18BP, or which have further advantages, like a better stability or a lower toxicity or immunogenicity, or they are easier to produce in large quantities, or easier to purify.

The sequences of IL-18BP and its splice variants/isoforms can be taken from WO 99/09063 or from Novick et al., 1999, as well as from Kim et al., 2000.

Functional derivatives of IL-18BP may be conjugated to polymers in order to improve the properties of the protein, such as the stability, half-life, bioavailability, tolerance by the human body, or immunogenicity. To achieve this goal, the functional derivative may comprise at least one moiety attached to one or more functional groups, which occur as one or more side chains on the amino acid residues. Such a functional group may e.g. be Polyethlyenglycol (PEG). PEGylation may be carried out by known methods, described in WO 92/13095, for example.

Therefore, in a preferred embodiment of the present invention, the inhibitors of IL-18, and in particular the IL-18BP is PEGylated.

In a further preferred embodiment of the invention, the inhibitor of IL-18 is a fused protein comprising all or part of an IL-18 binding protein, which is fused to all or part of an immunoglobulin. The person skilled in the art will understand that the resulting fusion protein retains the biological activity of IL-18BP, in particular the binding to IL-18. The fusion may be direct, or via a short linker peptide which can be as short as 1 to 3 amino acid residues in length or longer, for example, 13 amino acid residues in length. Said linker may be a tripeptide of the sequence E-F-M (Glu-Phe-Met), for example, or a 13-amino acid linker sequence comprising Glu-Phe-Gly-Ala-Gly-Leu-Val-Leu-Gly-Gly-Gln-Phe-Met introduced between the IL-18BP sequence and the immunoglobulin sequence. The resulting fusion protein has improved properties, such as an extended residence time in body fluids (half-life), increased specific activity, increased expression level, or the purification of the fusion protein is facilitated.

In a preferred embodiment, IL-18BP is fused to the constant region of an Ig molecule. Preferably, it is fused to heavy chain regions, like the CH2 and CH3 domains of human IgG1, for example. The generation of specific fusion proteins comprising IL-18BP and a portion of an immunoglobulin are described in example 11 of WO 99/09063, for example. Other isoforms of Ig molecules are also suitable for the generation of fusion proteins according to the present invention, such as isoforms $IgG_2$ or $IgG_4$, or other Ig classes, like IgM or IgA, for example. Fusion proteins may be monomeric or multimeric, hetero- or homomultimeric.

Interferons are predominantly known for inhibitory effects on viral replication and cellular proliferation. Interferon-γ, for example, plays an important role in promoting immune and inflammatory responses. Interferon β (IFN-β, an interferon type I), is said to play an anti-inflammatory role.

The invention therefore also relates to the use of a combination of an inhibitor of IL-18 and an interferon in the manufacture of a medicament for the treatment of CNS injury.

Interferons may also be conjugated to polymers in order to improve the stability of the proteins. A conjugate between Interferon β and the polyol Polyethlyenglycol (PEG) has been described in WO99/55377, for instance.

In another preferred embodiment of the invention, the interferon is interferon-β (IFN-β), and more preferably IFN-β1a.

The inhibitor of IL-18 production and/or action is preferably used simultaneously, sequentially, or separately with the interferon.

Tumor necrosis factor, has been described in the literature to have both protective and toxic effects in brain injury (Shohami et al., 1999). In Example 1 below, TNF injection into mice following severe brain trauma resulted in a significant decrease of IL-18 levels in the brain, thus indicating that TNF may have a beneficial effect on the recovery of traumatic brain injury. Therefore, a preferred embodiment of the invention relates to the use of an inhibitor of IL-18 in combination with TNF for the preparation of a medicament for treatment and/or prevention of brain injury, for simultaneous, sequential or separate use.

The combination of IL-18 inhibitors with TNF alpha is preferred in accordance with the present invention.

In a further preferred embodiment of the invention, the medicament further comprises an anti-inflammatory agent, such as an NSAID (nonsteroidal anti-inflammatory drugs). In a preferred embodiment, a COX-inhibitor, and most preferably a COX-2 inhibitor, is used in combination with an IL-18 inhibitor. COX-inhibitors are known in the art. Specific COX-2 inhibitors are disclosed in WO 01/00229, for example. The active components may be used simultaneously, sequentially, or separately.

Oxidative stress, in particular reactive oxygen species (ROS), have been described to play a role in the pathophysiology of brain damage (Shohami et al., 1997).

Therefore, in a preferred embodiment of the present invention, the medicament—further comprises an antioxidant, for simultaneous, sequential, or separate use. Many antioxidants are known in the art, such as vitamins A, C or E, or 5-aminosalicylic acid, or superoxide dismutase.

In a further preferred embodiment of the present invention, the inhibitor of IL-18 is used in an amount of about 0.001 to 100 mg/kg of body weight, or about 0.01 to 10 mg/kg of body weight or about 0.1 to 3 mg/kg of body weight or about 1 to 2 mg/kg of body weight.

In yet a further preferred embodiment, the inhibitor of IL-18 is used in an amount of about 0.1 to 1000 µg/kg of body weight or 1 to 100 µg/kg of body weight or about 10 to 50 µg/kg of body weight.

The invention further relates to the use of a nucleic acid molecule comprising the coding sequence of an IL-18 inhibitor, a mutein, functional derivative, or active fraction thereof, in the preparation of a medicament for the prevention and/or treatment of CNS injury.

Preferably, the nucleic acid molecule further comprises a sequence of an expression vector, e.g. to use gene therapy for administering the IL-18 inhibitor of the invention.

Preferably, the nucleic acid molecule is administered intramuscularly.

In order to treat and/or prevent CNS injury, the gene therapy vector comprising the sequence of an inhibitor of IL-18 production and/or action may be injected directly into the diseased tissue, for example, thus avoiding problems involved in systemic administration of gene therapy vectors, like dilution of the vectors, reaching and targeting of the target cells or tissues, and of side effects.

The use of a vector for inducing and/or enhancing the endogenous production of an inhibitor of IL-18 in a cell normally silent for expression of an IL-18 inhibitor, or which expresses amounts of the inhibitor which are not sufficient, are also contemplated according to the invention for treatment and/or prevention of CNS injury. The vector may comprise regulatory elements functional in the cells desired to express the inhibitor or IL-18. Such regulatory sequences or elements may be promoters or enhancers, for example. The regulatory sequence may then be introduced into the right locus of the genome by homologous recombination, thus operably linking the regulatory sequence with the gene, the expression of which is required to be induced or enhanced. The technology is usually referred to as "Endogenous Gene Activation" (EGA), and it is described e.g. in WO 91/09955.

It will be understood by the person skilled in the art that it is also possible to shut down IL-18 expression directly, without using an inhibitor of IL-18, with the same technique. To do that, a negative regulation element, like e.g. a silencing element, may be introduced into the gene locus of IL-18, thus leading to down-regulation or prevention of IL-18 expression. The person skilled in the art will understand that such down-regulation or silencing of IL-18 expression has the same effect as the use of an IL-18 inhibitor in order to prevent and/or treat disease.

The invention further relates to the use of a cell that has been genetically modified to produce an inhibitor of IL-18 in the manufacture of a medicament for the treatment and/or prevention of CNS injury.

The invention further relates to pharmaceutical compositions, particularly useful for prevention and/or treatment of inflammatory CNS injury, which comprise a therapeutically effective amount of an inhibitor of IL-18 and/or a therapeutically effective amount of an interferon and/or a pharmaceutically effective amount of TNF and/or a pharmaceutically effective amount of an anti-inflammatory agent and/or a pharmaceutically effective amount of an anti-oxidative agent.

As inhibitor of IL-18, the composition may comprise caspase-1 inhibitors, antibodies against IL-18, antibodies against any of the IL-18 receptor subunits, inhibitors of the IL-18 signaling pathway, antagonists of IL-18 which compete with IL-18 and block the IL-18 receptor, and IL-18 binding proteins, isoforms, muteins, fused proteins, functional derivatives, active fractions or circularly permutated derivatives thereof having the same activity.

IL-18BP and its isoforms, muteins, fused proteins, functional derivatives, active fractions or circularly permutated derivatives as described above are the preferred active ingredients of the pharmaceutical compositions.

The interferon comprised in the pharmaceutical composition is preferably IFN-beta or IFN-alpha.

In yet another preferred embodiment, the pharmaceutical composition comprises therapeutically effective amounts of TNF alpha. The pharmaceutical composition according to the invention may further comprise one or more COX-inhibitors.

The definition of "pharmaceutically acceptable" is meant to encompass any carrier, which does not interfere with effectiveness of the biological activity of the active ingredient and that is not toxic to the host to which it is administered. For example, for parenteral administration, the active protein(s) may be formulated in a unit dosage form for injection in vehicles such as saline, dextrose solution, serum albumin and Ringer's solution.

The active ingredients of the pharmaceutical composition according to the invention can be administered to an individual in a variety of ways. The routes of administration include intradermal, transdermal (e.g. in slow release formulations), intramuscular, intraperitoneal, intravenous, subcutaneous, oral, intracranial, epidural, rectal, topical, and intranasal routes. Any other therapeutically efficacious route of administration can be used, for example absorption through epithelial or endothelial tissues or by gene therapy wherein a DNA molecule encoding the active agent is administered to the patient (e.g. via a vector), which causes the active agent to be expressed and secreted in vivo. In addition, the protein(s) according to the invention can be administered together with other components of biologically active agents such as pharmaceutically acceptable surfactants, excipients, carriers, diluents and vehicles.

For parenteral (e.g. intravenous, subcutaneous, intramuscular) administration, the active protein(s) can be formulated as a solution, suspension, emulsion or lyophilized powder in association with a pharmaceutically acceptable parenteral vehicle (e.g. water, saline, dextrose solution) and additives that maintain isotonicity (e.g. mannitol) or chemical stability (e.g. preservatives and buffers). The formulation is sterilized by commonly used techniques.

The bioavailability of the active protein(s) according to the invention can also be ameliorated by using conjugation procedures which increase the half-life of the molecule in the human body, for example linking the molecule to polyethylenglycol, as described in the PCT Patent Application WO 92/13095.

The therapeutically effective amounts of the active protein (s) will be a function of many variables, including the type of antagonist, the affinity of the antagonist for IL-18, any residual cytotoxic activity exhibited by the antagonists, the route of administration, the clinical condition of the patient (including the desirability of maintaining a non-toxic level of endogenous IL-18 activity).

A "therapeutically effective amount" is such that when administered, the IL-18 inhibitor results in inhibition of the biological activity of IL-18. The dosage administered, as single or multiple doses, to an individual will vary depending upon a variety of factors, including IL-18 inhibitor pharmacokinetic properties, the route of administration, patient conditions and characteristics (sex, age, body weight, health, size), extent of symptoms, concurrent treatments, frequency of treatment and the effect desired. Adjustment and manipulation of established dosage ranges are well within the ability of those skilled in the art, as well as in vitro and in vivo methods of determining the inhibition of IL-18 in an individual.

According to the invention, the inhibitor of IL-18 is used in an amount of about 0.0001 to 100 mg/kg or about 0.01 to 10 mg/kg or body weight, or about 0.1 to 5 mg/kg of body weight or about 1 to 3 mg/kg of body weight or about 1 to 2 mg/kg of body weight. Alternatively, the IL-18 inhibitors may be administered in amounts of about 0.1 to 1000 µg/kg of body weight or about 1 to 100 µg/kg of body weight or about 10 to 50 µg/kg of body weight The route of administration, which is preferred according to the invention is administration by subcutaneous route. Intramuscular administration is further preferred according to the invention. In order to administer the IL-18 inhibitor directly to the place of its action, it is also preferred to administer it via the intracranial or intrathecal route. The intracranial route is especially preferred in combination with open head injury (missile injury of the brain).

In further preferred embodiments, the inhibitor of IL-18 is administered daily or every other day.

The daily doses are usually given in divided doses or in sustained release form effective to obtain the desired results. Second or subsequent administrations can be performed at a dosage which is the same, less than or greater than the initial or previous dose administered to the individual. A second or subsequent administration can be administered during or prior to onset of the disease.

According to the invention, the IL-18 inhibitor can be administered prophylactically or therapeutically to an individual prior to, simultaneously or sequentially with other therapeutic regimens or agents (e.g. multiple drug regimens), in a therapeutically effective amount, in particular with an interferon and/or a TNF and/or another anti-inflammatory agent, such as a COX inhibitor and/or an antioxidant. Depending on the brain injury, the co-administration of a TNF-antagonist instead of TNF itself can also be conceived (Shohami et al., 1999). Active agents that are administered simultaneously with other therapeutic agents can be administered in the same or different compositions.

The invention further relates to a method for the preparation of a pharmaceutical composition comprising admixing an effective amount of an IL-18 inhibitor and/or an interferon and/or a TNF antagonist and/or a COX inhibitor with a pharmaceutically acceptable carrier.

The invention further relates to a method of treatment of CNS injury, comprising administering a pharmaceutically effective amount of an IL-18 inhibitor to a patient in need thereof.

All references cited herein, including journal articles or abstracts, published or unpublished U.S. or foreign patent application, issued U.S. or foreign patents or any other references, are entirely incorporated by reference herein, including all data, tables, figures and text presented in the cited references. Additionally, the entire contents of the references cited within the references cited herein are also entirely incorporated by reference.

Reference to known method steps, conventional methods steps, known methods or conventional methods is not any way an admission that any aspect, description or embodiment of the present invention is disclosed, taught or suggested in the relevant art.

The foregoing description of the specific embodiments will so fully reveal the general nature of the invention that others can, by applying knowledge within the skill of the art (including the contents of the references cited herein), readily modify and/or adapt for various application such specific embodiments, without undue experimentation, without departing from the general concept of the present invention. Therefore, such adaptations and modifications are intended to be within the meaning an range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance presented herein, in combination with the knowledge of one of ordinary skill in the art.

Having now described the invention, it will be more readily understood by reference to the following examples that are provided by way of illustration and are not intended to be limiting of the present invention.

EXAMPLES

Materials and Methods

Trauma Model

The mice used in this study were males of age 8-16 weeks weighing 30-35 g. They were bred in a specific pathogen-free environment, kept under standard conditions of temperature and light in cages of 4-6 animals, and fed with food and water ad libitum. The study was performed according to the guidelines of the Institutional Animal Care Committee of the Hebrew University of Jerusalem, Israel. Experimental CHI was performed using the weight-drop device previously developed (Chen et al. 1996). Briefly, after induction of ether anesthesia, a midline longitudinal incision was performed, the skin was retracted and the skull exposed. The left anterior frontal area was identified and a tipped teflon cone was placed ~1 mm lateral to the midline, in the mid-coronal plane. The head was fixed and a 75 g weight was dropped on the cone from a height of 18 cm, resulting in a focal injury to the left hemisphere. After trauma, the mice received supporting oxygenation with 100% $O_2$ for no longer than 2 min, and were then brought back to their cages.

Assessment of IL-18 Levels in Mouse Brains

For quantification of intracranial IL-18 levels, mice of the C57BL/6 (B6) strain (total n=62) were assigned to six distinct groups: (1) "normal controls"; untreated B6 mice (n=10). (2) "ether anesthesia"; mice were anesthetized with ether for 10 minutes and decapitated after 24 h (n=10) or 7 days (n=10). (3) "sham operation"; these mice underwent anesthesia and longitudinal scalp incision and were sacrificed after 24 h (n=15) or 7 days. (4) "trauma group"; experimental CHI was performed as described above, and the animals were decapitated in ether anesthesia at 4 h (n=7), 24 h (n=7), and 7 days (n=7) after trauma. (5) "TNF injection"; for assessment of a possible role of TNF in the regulation of intracerebral IL-18, mice were ether anesthetized, injected intra-cerebro-ventricularly (i.c.v.) with 200 ng murine recombinant TNF (R&D Systems, Abingdon, UK) in 10 µl sterile phosphate-buffered saline (PBS) and sacrificed after 24 h (n=10). (6) "mock injection"; these animals were injected i.c.v. with vehicle only (10 µl sterile PBS) and sacrificed after 24 h (n=6), as a control group to the TNF-injected animals. In all mice, the brains were immediately removed after decapitation, snap-frozen in liquid nitrogen and stored at −70° C. until analysis. Brains from the trauma group were separated into left (ipsilateral) and right (contralateral) hemisphere, in order to allow a comparison of IL-18 levels in the injured vs. non-injured hemisphere. Tissue homogenization was performed with a Polytron (Kinematica, Kriens, Switzerland) using a dilution of 1:4 in ice cold extraction buffer (W/W) containing Tris 50 mM (pH 7.2), NaCI 150 mM, Triton-X-100 1% (Boehringer Mannheim, Rotkreuz, Switzerland), and protease inhibitor cocktail (Boehringer Mannheim). The homogenate was shaken on ice for 90 min and then centrifuged for 15 min at 3,000 g and 4° C. The supernatants were aliquoted and stored at −70° C. until analysis. The concentrations of total protein in the brain extracts were measured by Bradford assay (Bio Rad Laboratories, Munich, Germany) and found to be very constant in all mice assessed (12.1±2.1 mg/ml; mean±SD). Quantification of intracerebral cytokine levels was performed by ELISA specific for murine IL-18, according to the manufacturer's instructions (R&D Systems, Abingdon, UK). The sensitivity of the assay was 5 pg/ml. For comparison of the intracerebral IL-18 levels between the different animal groups, all concentrations below the detection limit of 5 pg/ml were assigned a value of 4.9 pg/ml. The samples were run undiluted in duplicate wells and the final concentration was calculated from the mean OD of duplicate samples. The OD was determined by spectrophotometer (Dynatech Laboratories Inc., Chantilly, Va.) at an extinction wavelength of 405 nm.

IL-18BP Treatment Protocol

Male Sabra mice of the Hebrew University strain (n=40) were used for the IL-18BP studies. Anesthesia and experimental CHI were performed as described above. For the treatment protocol, the animals were divided into two groups: In group A ("control group", n=16), mice were subjected to experimental CHI, injected with vehicle alone (PBS) after one hour, and observed for 7 days for neurological assessment (see below). In group B ("study group", n=18), the mice were injected i.p. with 50 µg IL-18BP immediately after determination of the neurological score at t=h after CHI. Since the blood-brain barrier permeability is 5-6-fold increased between 14 h post CHI, as previously determined in the same experimental model (Chen et al. 1996), IL-18BP is available to the brain under these conditions. Two additional groups of mice were treated according to groups A and B (group C: "control group"; group D: "study group", respectively) and decapitated after 48 h, followed by brain dissection for evaluation of posttraumatic edema, as described below.

Evaluation of Neurological Impairment

For assessment of posttraumatic neurological impairment, a Neurological Severity Score (NSS) has been previously developed and validated (Stahel et al., 2000).

The score consists of 10 individual clinical tasks on motor function, alertness, and physiological behavior, whereby one point is given for failure of the task and zero points for succeeding (Table 4). A maximal NSS of 10 points indicates severe neurological dysfunction, with failure of all tasks, whereas a score of zero is achieved by healthy uninjured mice. The NSS at 1 hour after trauma reflects the initial severity of injury and is highly correlated with clinical outcome (Beni-Adani et al. 2001). Evaluation of task performance was performed by two investigators who were blinded about the study groups at the time-points 1 h, 24 h, 72 h, and 7 days after experimental CHI. The ΔNSS, calculated as the difference between NSS at t=1 h and the NSS at any later time-point, is a parameter which reflects the degree of spontaneous recovery following brain injury, as described earlier (Chen et al. 1996).

TABLE 4

Neurological Severity Score (NSS) for head-injured mice.

| Task | Description | Points for success/fail |
|---|---|---|
| Exit circle | Ability and initiative to exit a circle of 30 cm diameter within 3 minutes. | 0/1 |
| Mono-/Hemiparesis | Paresis of upper and/or lower limb of the contralateral side. | 0/1 |
| Straight walk | Alertness, initiative, and motor ability to walk straight. | 0/1 |
| Startle reflex | Innate reflex; the mouse will bounce in response to a loud hand clap. | 0/1 |
| Seeking behavior | Physiological behavior as a sign of "interest" in the environment. | 0/1 |
| Beam balancing | Ability to balance on a beam of 7 mm width for at least 10 seconds. | 0/1 |
| Round stick balancing | Ability to balance on a round stick of 5 mm diameter for at least 10 seconds. | 0/1 |
| Beam walk: 3 cm | Ability to cross a 30 cm long beam | 0/1 |

TABLE 4-continued

Neurological Severity Score (NSS) for head-injured mice.

| Task | Description | Points for success/fail |
|---|---|---|
| | of 3 cm width. | |
| Beam walk: 2 cm | Same task, increased difficulty on a 2 cm wide beam. | 0/1 |
| Beam walk: 1 cm | Idem, increased difficulty on a 1 cm wide beam. | 0/1 |
| Maximal score | | 10 |

Assessment of Brain Edema

The extent of cerebral edema was evaluated by determining the tissue water content in the injured hemisphere, as previously described (Chen et al. 1996). Briefly, mice were anesthetized as described above at 48 h after trauma, which corresponds to a time-point at which edema is still significant in this model system (Chen et al. 1996). After decapitation, the cerebellum and brainstem were removed and a cortical segment of ~20 mg, from an area bordering the trauma site and from it contralateral hemisphere was prepared. The right (non-injured) hemisphere was used as an internal control. The tissue slices were weighed and dried for 24 h at 95° C. After weighing the "dried" sections, the percentage of brain water content was calculated as:

$$\%H_2O = [(\text{wet weight} - \text{dry weight}) \times 100]/\text{wet weight}.$$

Brain Injury Patients

Ten patients with isolated severe CHI (mean age±SD: 37±10 years; range 24-57 years; 9 males and one female), admitted to the Trauma Division of the University Hospital Zurich, were included in this study. All patients had a Glasgow Coma Scale (GCS) score≦8 after cardiopulmonary resuscitation (Teasdale and Jennett, 1974). Following CT scan evaluation, all patients received intraventricular catheters for therapeutic CSF drainage when the intracranial pressure (ICP) exceeded 15 mmHg. No patient was treated with steroids. Patients with multiple injuries requiring interventions for concomitant thoracic, abdominal, pelvic, spinal injuries, or long bone fractures were excluded from the study. The individual outcome was assessed using, the Glasgow Outcome Scale (GOS) (Jennett and Bond, 1975). The protocol for CSF and serum collection was approved by the Ethics Board Committee of the University Hospital, Zurich.

Sample Collection and IL-18 Analysis

The CSF and matched serum samples of CHI patients (n=10) were collected daily at one fixed time-point. Control CSF was collected from patients undergoing diagnostic spinal tap (n=5). These patients did not have signs of inflammatory CNS disease, based on normal CSF values of protein, glucose, and cell count (data not shown). In the CHI group, sample collection was performed for 10 days after trauma, unless the ventricular catheter was removed earlier, e.g. in cases where the ICP remained in a normal range (≦15 mmHg) for more than 24 hours. A total of 106 matched CSF and serum samples were collected in the trauma patients analyzed in this study. All samples were immediately centrifuged after collection, aliquoted and frozen at −70° C. until analysis. Quantification of IL-18 levels in CSF and serum was performed by ELISA specific for human IL-18 using commercially available kits (R&D Systems, Abingdon, UK). As for the murine assay, the sensitivity of the ELISA was 5 pg/ml, and the final IL-18 concentration was calculated from the mean OD determined in duplicate samples at an extinction wavelength of 405 nm. For comparison of the IL-18 CSF levels between CHI patients and controls, all concentrations below the detection limit of 5 pg/ml were assigned a value of 4.9 pg/ml.

Data Analysis

Statistical analysis of the data was performed on commercially available software (SPSS 9.0 for Windows™). The non-parametric Mann-Whitney-U test was used for analysis of data which were not normally distributed, such as the neurological scores (NSS and ΔNSS). The unpaired Student's t-test was used for comparison of intracerebral IL-18 concentrations in the different mouse groups and for analysis of differences in brain water content in the IL-18BP-treated vs. vehicle-injected mice. The comparison of human IL-18 levels, either in daily CSF vs. matched serum samples in CHI patients, or in trauma vs. control CSF, were determined using the general linear model for repeated measures ANOVA. A p-value<0.05 was considered to be statistically significant.

Results

Example 1

Intracerebral IL-18 Levels in Mice

As shown in FIG. 1, IL-18 was detectable by ELISA in brain homogenates of untreated ("normal") control mice of the B6 strain (n=10), with a mean level of 27.7±1.7 [±SEM] ng/ml. In the experimental groups, the induction of ether anesthesia alone or in combination with "sham" operation (i.e. ether anesthesia and longitudinal scalp incision) resulted in significantly elevated intracranial IL-18 levels of 48.9±1.1 ng/ml ("ether" group, n=8) and 54.3±2.7 ng/ml ("sham" group, n=13), respectively (p<0.01 vs. "normal" mice, unpaired Student's t-test; FIG. 1). The difference between the "ether" and "sham"-treated animals was not statistically significant (p=0.16).

In the trauma group (n=21), induction of CHI resulted in elevated IL-18 levels both in the injured and in the contralateral hemisphere within 4 h (60.6±3.3 and 59.8±5.0 ng/ml, respectively) to 24 h (56.9±2.1 and 56.3±3.7 ng/ml, respectively) after trauma, however, the levels were not significantly higher compared to the "ether" or "sham" groups (p>0.05).

In contrast to this, by 7 days after CHI, a significant increase of the intracerebral IL-18 concentration was detected in the injured hemisphere, as compared to ether-anesthetized or sham-operated animals (67.6±5.1 ng/ml vs. 42.2±0.8 and 45.2±0.5 ng/ml, respectively; p<0.01), whereas the IL-18 levels in the contralateral hemisphere were not significantly elevated above these two control groups (63.2±6.0 ng/ml; p=0.06).

In order to assess the role of TNF, a crucial mediator of inflammation in this trauma model (Shohami et al. 1999), with regard to the regulation of intracerebral IL-18 levels, an additional group of B6 mice (n=10) were injected i.c.v. with 200 ng murine recombinant TNF in 10 μl sterile PBS and sacrificed after 24 h. As shown in FIG. 1, "mock" injection with vehicle only (n=6) resulted in a significant up-regulation of intracerebral IL-18 within 24 h, as compared to untreated normal B6 mice (53.6±3.9 vs. 27.7±1.7 ng/ml; p<0.001).

The injection of TNF induced a significant attenuation of IL-18 levels in the intracranial compartment within 24 h (22.1±6.9 ng/ml; n=10), as compared to the "moc"-injected control group 24 h (53.6±3.9 ng/ml; p<0.001). The IL-18 levels in the "TNF group" were even lower than in untreated normal mice (27.7±1.7 ng/ml), although in this case the difference was not statistically significant (p=0.45).

Example 2

Effect of IL-18BP Treatment on the Neurological Recovery After Trauma

In order to investigate the hypothesis that inhibition of IL-18 might facilitate recovery in brain injury, recovery at different time points after a single injection of IL-18BP was compared. It was previously shown that the Neurological Severity Score (NSS) at 1 h following trauma reflects most accurately the magnitude of the trauma and correlates with the volume of the injured tissue as seen in MRI and in histology.

Figure 2:
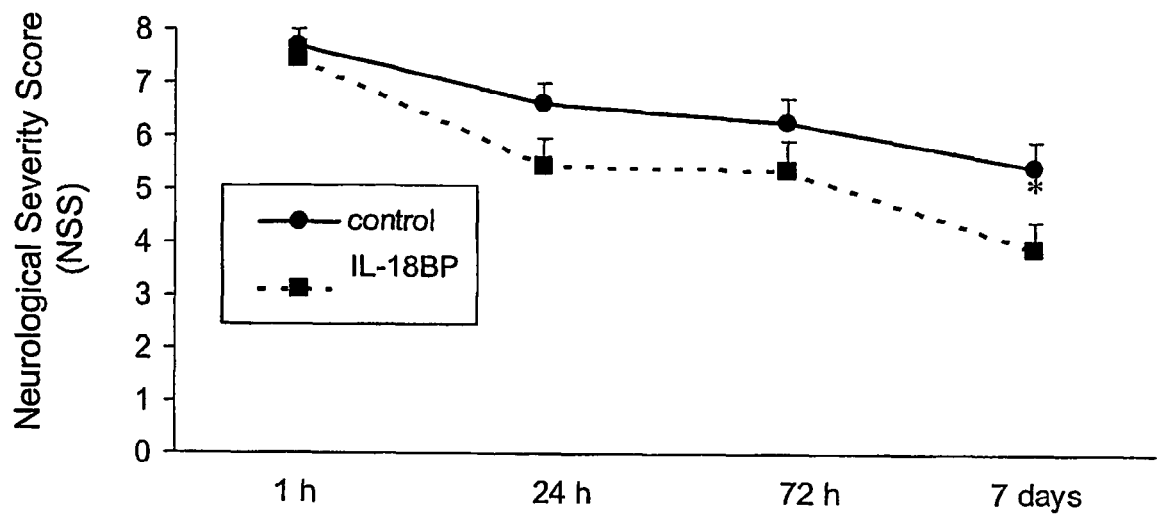
FIG. 2 shows the development of NSS (Neurological Severity Score) measured 1 hour (h), 24 h, 72 h or 168 h following trauma, either with 50 µg of IL-18BP administered i.p. at 1 h following trauma (squares), or with injection of vehicle only (control, circles).

In order to obtain groups of animals with comparable trauma, mice were assigned to different treatment groups after their initial NSS was evaluated at t=1 h. As shown in FIG. 2 (NSS in IL-18BP (squares) vs. Control (circles) both groups had a similar initial NSS(1 h) (7.69±0.3023 and 7.44±0.3627 control and IL-18BP respectively) indicating comparable severity of injury.

Evaluation of NSS at later times (1-7 days) revealed that animals treated intraperitoneally (i.p.) with IL-18BP exhibit considerably less neurological damage, as evident by NSS values, that reached significance at 7 days post trauma (p=0.045).

Figure 3:
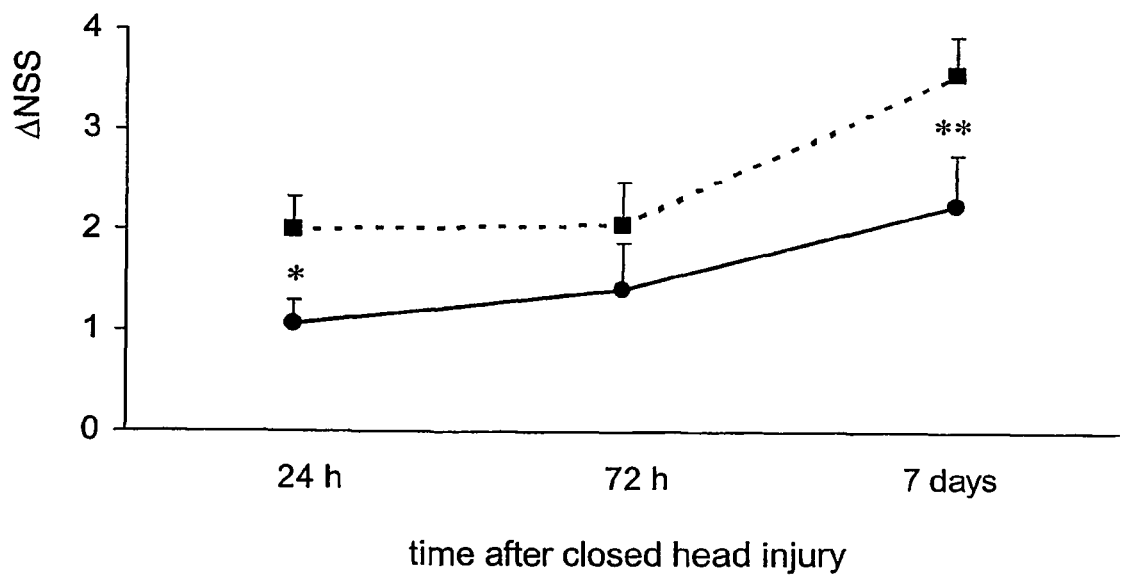
FIG. 3 shows the ΔNSS measured 24 h, 72 h or 168 h following trauma, either with 50 µg of IL-18BP administered i.p. at 1 h following trauma (squares), or with injection of vehicle only (control, circles).

The rate of recovery, expressed as ΔNSS (t)=NSS (1 h)−NSS (t), was calculated. A higher value of ΔNSS reflects greater recovery and a zero or negative ΔNSS reflects no recovery or worsening. FIG. 3 depicts the ΔNSS values of the two groups. At two time points, both at 24 h and at 7d the difference between the average ΔNSS values reached significance.

Another experiment was carried out to investigate whether treatment with IL-18BP, given at 3 days post injury can be effective. The issue of timing of treatment is critical, and so far therapy was shown to be effective when given beyond a few hours. Since it had been found that IL-18 itself rises at 7d post-trauma, and treatment with IL-18BP given at 1 h post-trauma led to greatest effect also at day 7, it was decided now to treat the mice at day 3 post injury. For comparison, another group was treated at 1 h and at 3d with IL-18BP. The control group was treated with the solvent (vehicle) only.

Figure 4:
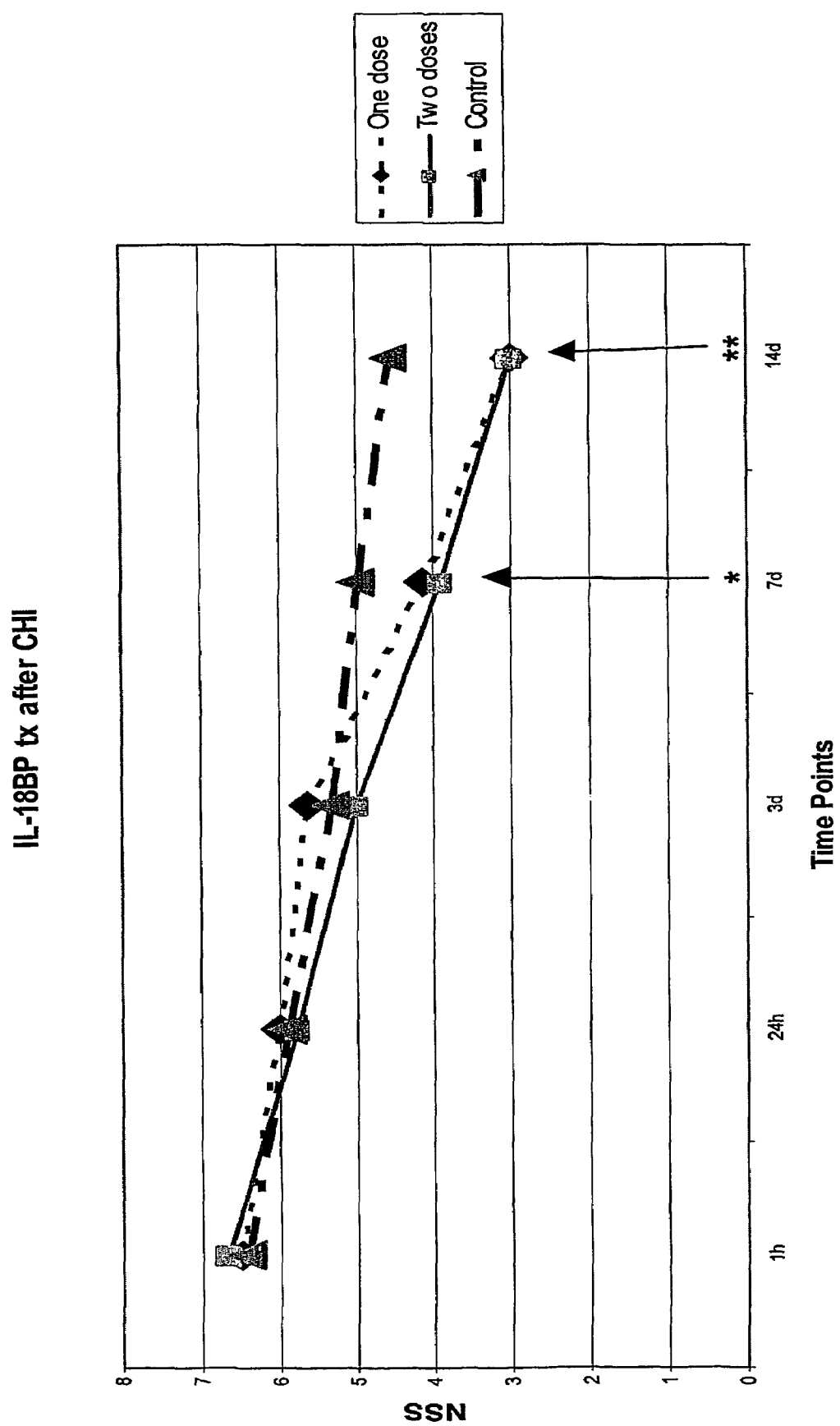
FIG. 4 shows the ΔNSS measured 1 h, 24 h, 3 days (d), 7d or 14d following trauma, either with 50 µg of IL-18BP administered i.p. either as a single dose at 3d following trauma (diamonds), or with a double dose at 1 h and 3d following trauma (squares) or injection of vehicle only (control, triangle).

The results of this experiment are depicted in FIG. 4, from which it is clear that a single treatment given at day 3 is as effective as that given one hour after CHI and again at 3 days.

This experiment demonstrates the dramatic beneficial effect of a one-time administration of IL-18BP, either given 1 h or 3 days after closed head injury, on recovery from traumatic head injury in an experimental murine model.

Example 3

Elevated IL-18 Levels in Human CSF after Brain Injury

IL-18 levels were assessed in daily CSF and serum samples from 10 patients with severe CHI for up to 10 days after trauma. The patients' demographic and clinical data are presented in Table 5.

TABLE 5

| | Demographic and clinical data of patients with severe CHI[a] | | | | | | |
|---|---|---|---|---|---|---|---|
| | | | | IL-18 in CSF[d] (pg/ml) | | IL-18 in serum (pg/ml) | |
| Patient No. | Age (years)/ gender | GCS[b] | GOS[c] | median | [range][e] | median | [range][e] |
| 1 | 48/m | 3 | 1 | 283 | [78-966] | 57.5 | [12-66] |
| 2 | 31/m | 7 | 4 | 228.4 | [22-745] | 19.7 | [4.9-108] |
| 3 | 26/m | 5 | 3 | 208.5 | [20-392] | 37.2 | [14-163] |
| 4 | 57/m | 5 | 4 | 72.6 | [30-286] | 48.9 | [14-104] |
| 5 | 24/m | 4 | 5 | 32.6 | [4.9-155] | 17 | [4.9-58] |
| 6 | 36/m | 8 | 1 | 49.4 | [10-290] | 16.7 | [12-67] |
| 7 | 38/f | 3 | 4 | 17.9 | [11-100] | 13 | [4.9-46] |
| 8 | 35/m | 3 | 3 | 69.8 | [4.9-329] | 19.8 | [7-77] |
| 9 | 37/m | 3 | 4 | 37 | [23-75] | 57.3 | [25-98] |
| 10 | 41/m | 7 | 5 | 4.9 | [4.9-169] | 26.2 | [15-38] |
| Control CSF (n = 5) | | | | 4.9 | [4.9-7.8] | | |

[a]CHI, closed head injury
[b]GCS, Glasgow Coma Score (Teasdale and Jennett, 1974).
[c]GOS = Glasgow Outcome Score at 3 months after injury;
5 = asymptomatic,
4 = moderate disability,
3 = severe disability,
2 = persistant vegetative state,
1 = death (Jennett and Bond, 1975).
[d]CSF = cerebrospinal fluid.
[e]IL-18 levels below the detection limit of 5 pg/ml were assigned a value of 4.9 pg/ml.

As shown in Table 5, the intrathecal IL-18 levels were significantly elevated in 9/10 CHI patients, as compared to control CSF from 5 patients without trauma or inflammatory neurological disease (p<0.05; repeated measures ANOVA). Only one patient #10) had IL-18 CSF levels, which were not significantly elevated as compared to control CSF (p=0.31). The median levels and individual ranges of IL-18 in CSF and serum are presented in Table 5.

Notably, the maximal IL-18 concentrations in CSF (966 ng/ml) were up to 200-fold higher in head-injured patients than in controls. Intracerebral IL-18 was detectable by ELISA in 90% of all CSF samples in the trauma group, whereas only 40% control CSF samples had detectable intracerebral IL-18 levels (i.e. >4.9 ng/ml). In 8/10 CHI patients, the median IL-18 concentrations were significantly higher in CSF than in serum (p<0.05; repeated measures ANOVA). However, in two patients (#9, 10) the median IL-18 levels in serum exceed the corresponding concentrations in CSF, as shown in Table 5.

These results show that there are significantly elevated levels of IL-18 in the cerebrospinal fluid of traumatic head injury patients. The addition of IL-18BP may reduce these elevated levels, and may thus exert its beneficial effect on recovery from closed head injury, as shown in Example 2 above.

REFERENCES

1. Altschul S F et al, J Mol Biol, 215, 403-410, 1990, Altschul S F et al, Nucleic Acids Res., 25:389-3402, 1997
2. Chater, K. F. et al., in "Sixth International Symposium on Actinomycetales Biology", Akademiai Kaido, Budapest, Hungary (1986), pp. 45-54).
3. Chen, Y., S. Constantini, V. Trembovler, M. Weinstock, and E. Shohami. 1996. An experimental model of closed head injury in mice: pathophysiology, histopathology, and cognitive deficits. J. Neurotrauma 13:557-68
4. Conti, C. B., N.Y. Calingasan, Y. Kim, H. Kim, Y. Bae, E. Gibson, and T. H. Joh. 1999. Cultures of astrocytes and microglia express interleukin-18. Mol. Brain Res. 67:46-52
5. Conti, B., J. W. Jahng, C. Tinti, J. H. Son, and T. H. Joh. 1997. Induction of interferon-gamma inducing factor in the adrenal cortex. J. Biol. Chem. 272:2035-2037.
6. Culhane, A. C, M. D. Hall, N. J. Rothwell, and G. N. Luheshi. 1998. Cloning of rat brain interleukin-18 cDNA. Mol. Psychiatry 3:362-6
   a. Devereux J et al, Nucleic Acids Res, 12, 387-395, 1984.
7. DiDonato, J A, Hayakawa, M, Rothwarf, D M, Zandi, E and Karin, M. (1997), Nature 388, 16514-16517.
8. Elliott, M. J., Maini, R. N., Feldmann, M., Long-Fox, A., Charles, P., Bijl, H., and Woody, J. N., 1994, Lancet 344, 1125-1127.
9. Fassbender, K., O. Mielke, T. Bertsch, F. Muehlhauser, M. Hennerici, M. Kurimoto, and S. Rossol. 1999. Interferon γ-inducing factor (IL-18) and interferon-γ in inflammatory CNS diseases. Neurology 53:1104-6
10. Jander, S., and G. Stoll. 1998. Differential induction of interleukin-12, interleukin-18, and interleukin-1β coverting enzyme mRNA in experimental autoimmune encephalomyelitis of the Lewis rat. J. Neuroimmunol. 91:93-9
11. Lancet 1975 Mar. 1; 1(7905):480-4. Jenneft B, Bond M.
12. Izaki, K. (1978) Jpn. J. Bacteriol. 33:729-742).
13. Kim S H, Eisenstein M, Reznikov L, Fantuzzi G, Novick D, Rubinstein M, Dinarello C A. Structural requirements of six naturally occurring isoforms of the IL-18 binding protein to inhibit IL-18. Proc Natl Acad Sci U S A 2000; 97:1190-1195.
14. Kossmann, T., P. F. Stahel, P. M. Lenzlinger, H. Redl, R. W. Dubs, O. Trentz, G. Schlag, and M. C. Morganti-Kossmann. 1997. Interleukin-8 released into the cerebrospinal fluid after brain injury is associated with blood brain-barrier dysfunction and nerve growth factor production. J. Cereb. Blood Flow Metab. 17:280-9
15. Knight D M, Trinh H, Le J, Siegel S, Shealy D, McDonough M, Scallon B, Moore M A, Vilcek J, Daddona P, et al. Construction and initial characterization of a mouse-human chimeric anti-TNF antibody. Mol Immunol 1993 Nov. 30: 16 1443-53
16. Maliszewski, C. R., T. A. Sato, T. Vanden Bos, S. Waugh, S. K. Dower, J. Slack, M. P. Beckmann, and K. H. Grabstein. 1990. Cytokine receptors and B cell functions. I. Recombinant soluble receptors specifically inhibit IL-1- and IL-4-induced B cell activities in vitro. J. Immunol. 144:3028-3033.
17. Micallef, M. J., T. Ohtsuki, K. Kohno, F. Tanabe, S. Ushio, M. Namba, T. Tanimoto, K. Torigoe, M. Fujii, M. Ikeda, S. Fukuda, and M. Kurimoto. 1996. Interferon-gamma-inducing factor enhances T helper 1 cytokine production by stimulated human T cells: synergism with interleukin-12 for interferon-gamma production. Eur-J-Immunol 26:1647-51 issn: 0014-2980.
18. Morganti-Kossmann, M. C., P. M. Lenzlinger, V. Hans, P. Stahel, E. Csuka, E. Ammann, R. Stocker, O. Trentz, and T. Kossmann. 1997. Production of cytokines following brain injury: beneficial and deleterious for the damaged tissue. Mol. Psychiatry 2:133-6
19. Nakamura K, Okamura H, Wada M, Nagata K, Tamura T. Infect Immun 1989 February; 57(2):590-5
20. Novick, D, Kim, S-H, Fantuzzi, G, Reznikov, L, Dinarello, C, and Rubinstein, M (1999). Immunity 10, 127-136.
21. Okamura H, Nagata K, Komatsu T, Tanirn-oto T, Nukata Y, Tanabe F, Akita K, Torigoe K, Okura T, Fukuda S, et al. Infect Immun 1995 October; 63(10):3966-72
22. Parnet, P, Garka, K E, Bonnert, T P, Dower, S K, and Sims, J E. (1996), J. Biol. Chem. 271, 3967-3970.
    a. Pearson W R, Methods in Enzymology, 183, 63-99, 1990
    b. Pearson W R and Lipman D J, Proc Nat Acad Sci USA, 85, 2444-2448, 1988
23. Prinz, M., and U. K. Hanisch. 1999. Murine microglial cells produce and respond to interleukin-18. J. Neurochem. 72:2215-8
24. J Clin Invest 1997 Feb. 1; 99(3):469-74 Rothe H, Jenkins N A, Copeland N G, Kolb H.
25. Scherbel, U., R. Raghupathi, M. Nakamura, K. E. Saatman, J. Q. Trojanowski, E. Neugebauer, M. W. Marino, and T. K. Mcintosh. 1999. Differential acute and chronic responses of tumor necrosis factor-deficient mice to experimental brain injury. Proc. Natl. Acad. Sci. USA 96:8721-6
26. Shohami, E., I. Ginis, and J. M. Hallenbeck. 1999. Dual role of tumor necrosis factor alpha in brain injury. Cytokine Growth Factor Rev. 10:119-30
27. Shohami, E; Beit-Yannai E., Horowitz M; Kohen R (1997): J. Cereb. Blood Flow Metab. 17, 1007-1019.
28. Teasdale G, Jennett B. Lancet 1974 Jul. 13; 2(7872):81-4
29. Stahel P F, Shohami E, Younis F M, Kariya K, Otto V I, Lenzlinger P M, Grosjean M B, Eugster H P, Trentz O, Kossmann T, Morganti-Kossmann M C. J Cereb Blood Flow Metab 2000 February; 20(2):369-80
30. Ushio S, Namba M, Okura T, Hattori K, Nukada Y, Akita K, Tanabe F, Konishi K, Micallef M, Fujii M, Torigoe K, Tanimoto T, Fukuda S, Ikeda M, Okamura H, Kurimoto M. J Immunol 1996 Jun. 1; 156(11):4274-9
31. Wheeler, R. D., A. C. Culhane, M. D. Hall, S. Pickering-Brown, N. J. Rothwell, and G. N. Luheshi. 2000. Detection of the interleukin-18 family in rat brain by RT-PCR. Mol. Brain Res. 77:290-3
32. Whalen, M. J., T. M. Carlos, P. M. Kochanek, S. R. Wisniewski, M. J. Bell, R. S. Clark, S. T. DeKosky, D. W. Marion, and P. D. Adelson. 2000. Interleukin-8 is increased in cerebrospinal fluid of children with severe head injury. Crit. Care Med. 28:929-34
33. Yoshimoto T, Takeda, K, Tanaka, T, Ohkusu, K, Kashiwamura, S, Okamura, H, Akira, S and Nakanishi, K (1998), J. Immunol. 161, 3400-3407.

The invention claimed is:
1. A method of treatment of an isolated closed head injury comprising administering to an individual in need thereof an effective inhibiting amount of IL-18BP, wherein the IL-18BP is administered in a single dose at 3 days after the closed head injury.

2. A method for the treatment of an isolated closed head injury comprising administering to an individual in need thereof an effective amount of IL-18BP and a pharmaceutically acceptable carrier, and wherein the IL-18BP is administered in a single dose at 3 days after the closed head injury.

3. The method of claim 1 or 2, wherein the IL-18BP inhibitor is used in an amount of about 0.01 to 10 mg/kg of body weight.

4. The method of claim 1 or 2, wherein the IL-18BP inhibitor is used in an amount of about 0.01 to 10 mg/kg of body weight.

5. The method of claim 1 or 2, wherein the IL-18BP inhibitor is used in an amount of about 0.1 to 5 mg/kg body weight.

6. The method of claim 1 or 2, wherein the IL-18BP inhibitor is used in an amount of about 1 to 3 mg/kg of body weight.

7. The method according to claim 1 or 2, wherein the IL-18BP inhibitor is administered subcutaneously.

8. The method according to claim 2, wherein the IL-18BP is glycosylated at least at one site.

9. The method according to claim 2, wherein the IL-18BP comprises an immunoglobulin (Ig) fusion.

10. The method according to claim 2, wherein the IL-18BP comprises at least one moiety attached to at least one functional group which occur as one or more side chains on the amino acid residues, wherein the moiety is a polyethylene glycol (PEG).

11. The method according to claim 2, further comprising administering to the individual in need thereof simultaneously, sequentially, or separately an anti-inflammatory agent.

12. The method according to claim 11, wherein the anti-inflammatory agent is a COX-inhibitor.

13. The method according to claim 2, further comprising administering to the individual in need thereof simultaneously, sequentially, or separately an antioxidant.

* * * * *

UNITED STATES PATENT AND TRADEMARK OFFICE
CERTIFICATE OF CORRECTION

| | | |
|---|---|---|
| PATENT NO. | : 7,655,616 B2 | Page 1 of 1 |
| APPLICATION NO. | : 10/478614 | |
| DATED | : February 2, 2010 | |
| INVENTOR(S) | : Esther Shohami | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 444 days.

Signed and Sealed this

Twenty-third Day of November, 2010

David J. Kappos
*Director of the United States Patent and Trademark Office*